United States Patent [19]

Schönbächler et al.

[11] Patent Number: 5,522,806
[45] Date of Patent: Jun. 4, 1996

[54] SELF-CLOSING CATHETER VALVE

[76] Inventors: Peter Schönbächler, Oberseeburg 41, CH-6006 Luzern; Peter Huser, Lindenhöhe 5, CH-6045 Meggen; Thomas Huser, Weidtobelweg 3, CH-6045 Meggen; Othmar Horat, Hofmattstrasse 25, CH-6033 Buchrain, all of Switzerland

[21] Appl. No.: 190,025

[22] PCT Filed: May 28, 1993

[86] PCT No.: PCT/CH93/00140

§ 371 Date: Mar. 2, 1994

§ 102(e) Date: Mar. 2, 1994

[87] PCT Pub. No.: WO93/24173

PCT Pub. Date: Dec. 9, 1993

[30] Foreign Application Priority Data

Jun. 2, 1992 [CH] Switzerland ............... 1766/92
Sep. 11, 1992 [CH] Switzerland ............... 2877/92

[51] Int. Cl.[6] .............. A61M 5/00; A61M 1/00; F16K 7/04
[52] U.S. Cl. .............. 604/250; 604/34; 251/7
[58] Field of Search .............. 604/30, 31, 34, 604/246, 250, 283, 905; 251/7, 342

[56] References Cited

U.S. PATENT DOCUMENTS

| | | | |
|---|---|---|---|
| 2,709,542 | 5/1955 | Eller et al. | 251/7 |
| 3,985,140 | 10/1976 | Harris | 604/250 |
| 4,097,020 | 6/1978 | Sussman | 251/342 |
| 4,245,812 | 1/1981 | Burger | 251/10 |
| 4,407,434 | 10/1983 | Kempf | 251/7 |
| 5,059,186 | 10/1991 | Yamamoto | 604/280 |
| 5,257,978 | 11/1993 | Haber et al. | 604/250 |
| 5,437,642 | 8/1995 | Thill et al. | 604/153 |

FOREIGN PATENT DOCUMENTS

| | | |
|---|---|---|
| 0008064 | 2/1980 | European Pat. Off. . |
| 0455478 | 11/1991 | European Pat. Off. . |
| 2590645 | 5/1987 | France ............... 604/250 |

*Primary Examiner*—John D. Yasko
*Assistant Examiner*—Adam J. Cermak
*Attorney, Agent, or Firm*—Speckman, Pauley & Fejer

[57] ABSTRACT

A self-closing catheter valve having a housing with an oval cross section and a conical hose attachment connector which can be inserted into a catheter hose. A valve hose piece partially extends through the housing. A V-shaped spring element deforms and constricts the valve hose piece by pressing the valve hose piece against a wall of the housing. An actuation member is positioned within the housing for bringing the self-closing catheter valve into an open position.

7 Claims, 3 Drawing Sheets

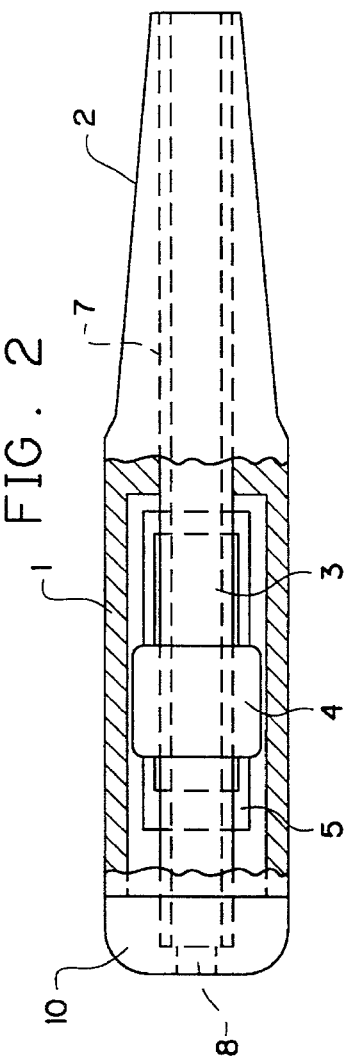
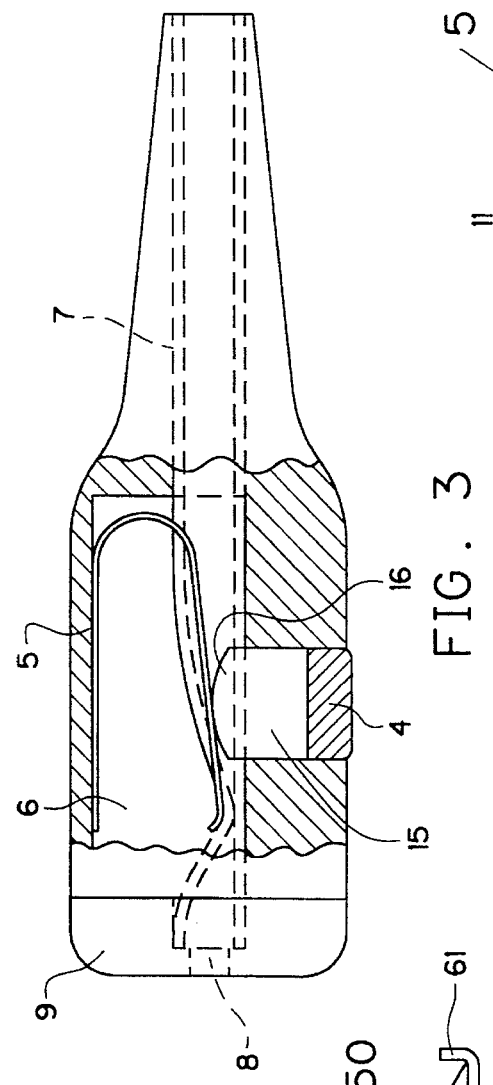
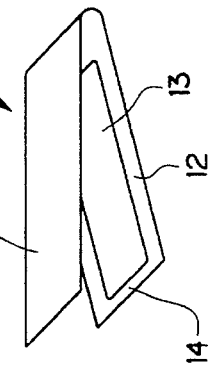
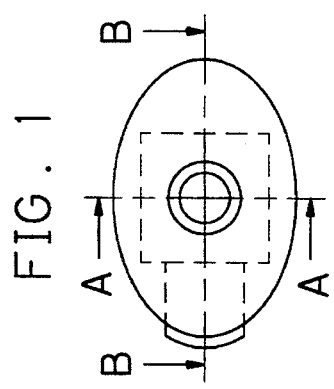
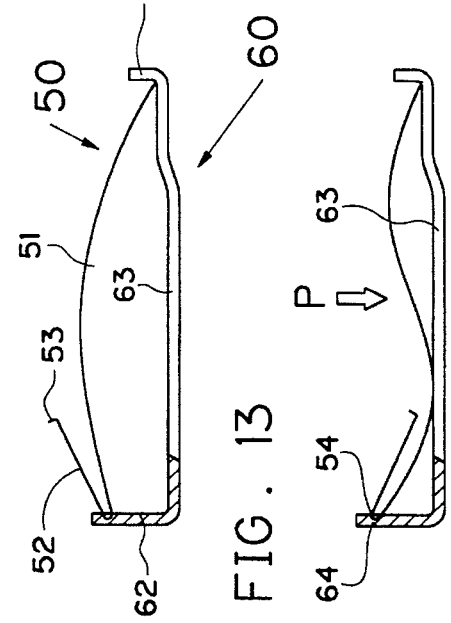

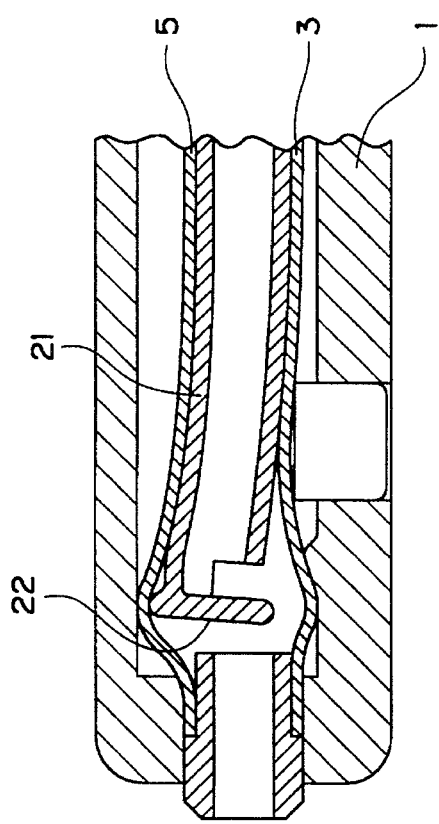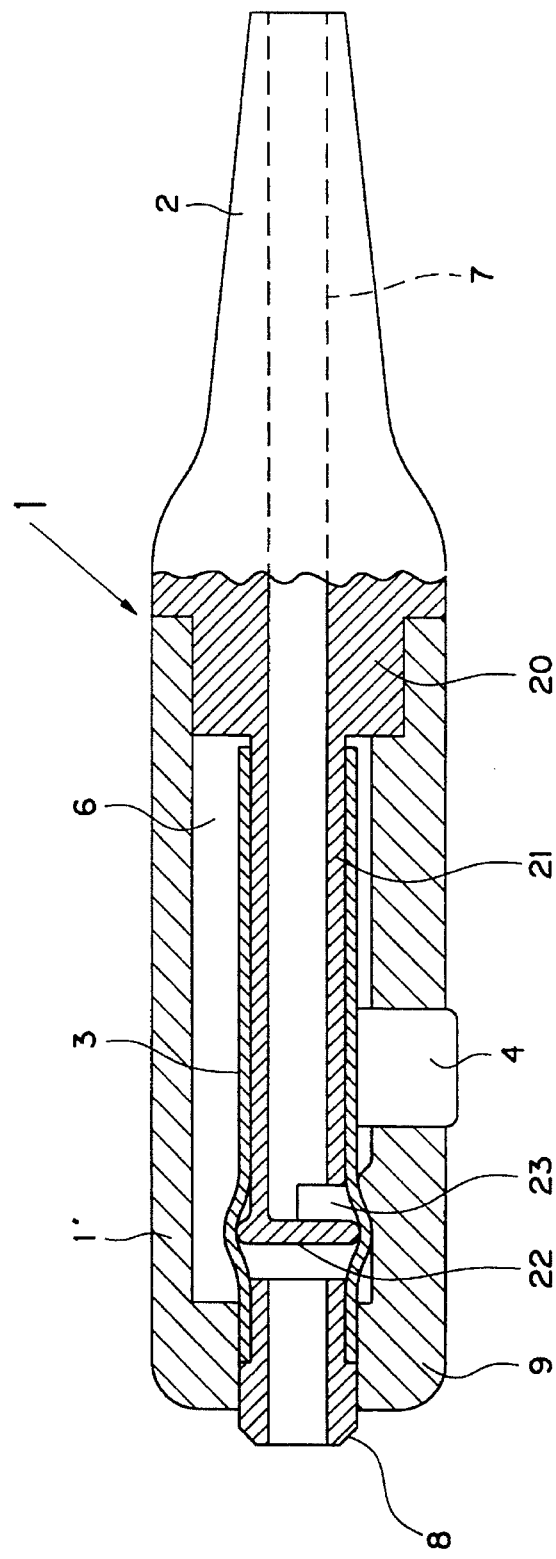

SELF-CLOSING CATHETER VALVE

BACKGROUND OF THE INVENTION

1. Field of the Invention

This invention relates to a self-closing catheter valve having a housing with an oval cross section and a conical hose attachment connector which can be inserted into a catheter hose, a valve hose piece which partially extends through the housing, an actuating member positioned within the housing for bringing the self-closing catheter valve into an open position, and a spring element for deforming and constricting the valve hose piece.

2. Description of Prior Art

Conventional catheter valves are known in a great number of embodiments and are commercially available. Only the valves which are used outside of a body are of interest in connection with this invention. The following publications are cited to provide examples of such valves: European Patent reference EP-A-O 455 478, German Patent reference DE-A-39 09 63.4, and German Patent reference DE-A-40 29 05.3.

The catheter valves employed in urology are increasingly being used to treat chronic patients. In geriatrics in particular, patients must use catheter valves for years. However, this fact had scarcely been taken into account up to now. If these factors are taken into consideration, a list of requirements can be compiled which contains at least the following:

1. The valve must be ergonomically shaped, so that the patient does not get sores from the valve rubbing against him, even if he is confined to a bed for a long time;
2. Because the cost of care is particularly important with long-term patients, the catheter valve must be extremely inexpensive;
3. The motor responses of geriatric patients are often reduced, requiring the catheter valve to be extremely simple and operable with only one hand; and
4. long-term use requires that the entire valve can be rinsed without being disassembled and that the entire valve can be sterilized.

To meet these requirements it is necessary to take aspects of shape into consideration as well as structural aspects which in part are also dictated by the shape.

This invention can be distinguished from the catheter valve taught by European Patent reference EP-B-0 088 871. The self-closing catheter valve of the '871 European Patent reference has a housing with a conical hose attachment connector on which a catheter hose can be pushed, a valve hose piece which at least partially extends through the housing, and an actuating member for bringing the valve into an open position. The catheter valve of the '871 European Patent reference operates with a hose attachment connector displaceably seated in the housing. The valve hose piece is crimped by this displacement. The automatic closing function of the catheter valve is achieved by a pressure spring which is pushed over the connector along the hose attachment connector in an area inside the housing. To disconnect the hose from the catheter valve, the patient must pull these two parts apart against the force of the pressure spring. This cannot be accomplished with one hand. To reduce the unwieldiness of the two-handed operation the hose attachment connector is rotatable with respect to the housing and can therefore be locked in an open position. Because the hose attachment connector can be locked in an open position, the catheter valve is no longer self-locking. The hose attachment connector has to be moved out of the locked position before the catheter valve can become self-locking. Based on these structural conditions the catheter valve is cylindrical.

The disadvantage of two-handed operation has been recognized and the catheter valve has been changed in such a way that one-handed operation is possible. Such a modified catheter valve is commercially available and has a rocking arm seated on the housing for forcing the hose attachment connector out of the housing against the force of the spring. However, long-term patients are quickly rubbed raw by this arm.

Furthermore, the originally relatively complex valve which has seven components requires additional components because of this modification.

SUMMARY OF THE INVENTION

It is an object of this invention to provide a self-closing catheter valve having a housing with an oval cross section and a conical hose attachment connector which can be inserted into a catheter hose, a valve hose piece which partially extends through the housing, an actuating member positioned within the housing for bringing the self-closing catheter valve into an open position, and a spring element for deforming and constricting the valve hose piece, which can be easily operated with one hand, which is relatively simple and requires relatively few components, which is ergonomically shaped, which is inexpensive, and which can be sterilized and reused.

This and other objects are achieved by a self-closing catheter valve in which a spring element having a V-shaped spring is positioned within a chamber of a housing. A surface of a first spring leg of the V-shaped spring abuts against the housing. A second spring leg of the V-shaped spring has a recess wide enough to accommodate a valve hose piece positioned within the housing. The recess is bordered by an end bar on a free end of the second spring leg and two longitudinal bars of the second spring leg which support the end bar. The end bar clamps the valve hose piece against the housing. An actuation member, which in one preferred embodiment of this invention is a button, abuts the two longitudinal bars of the second spring leg. According to one preferred embodiment of this invention the housing has first and second plastic sections. The first plastic section has a hose attachment connector and a chamber wall. The second plastic section has a cap, which, together with the chamber wall of the first plastic section, defines the chamber. An end of the valve hose piece is attached to the cap and positioned within a urine outlet opening formed in the cap.

The self-closing catheter valve according to one preferred embodiment of this invention is suitable for use with a urine collecting bag because such use requires frequent disassembly of the self-closing catheter valve. Accordingly, a plug element may be used to connect a suitable hose plug to an end wall of the housing. The plug element may comprise a central tube surrounded by an annular conduit of the housing. The annular conduit has radial projections for locking the hose plug to the housing. Furthermore, according to this preferred embodiment, it is possible to relieve the hose when the catheter valve is stored so that the spring does not press on the hose.

BRIEF DESCRIPTION OF THE DRAWINGS

The self-closing catheter valve of this invention will be described below in connection with the drawings wherein:

FIG. 1 is a top view of a self-closing catheter valve, according to one preferred embodiment of this invention;

FIG. 2 is a partial sectional view of the self-closing catheter valve taken along line A—A, as shown in FIG. 1;

FIG. 3 is a partial sectional view of the self-closing catheter valve taken along line B—B, as shown in FIG. 1;

FIG. 3a is a perspective view of a spring element, according to one preferred embodiment of this invention;

FIG. 4 is a partial sectional view of a self-closing catheter valve taken along line B—B, according to another preferred embodiment of this invention;

FIG. 5 is a cross-sectional view of a portion of the self-closing catheter valve shown in FIG. 4, in an open position;

FIG. 12 is a partial cross-sectional side view of a spring element positioned in a spring holder in an actuated position, according to one preferred embodiment of this invention; and FIG. 13 is a partial cross-sectional side view of the spring element shown in FIG. 12 positioned in the spring holder in a loaded position.

DESCRIPTION OF PREFERRED EMBODIMENTS

Figure 6:
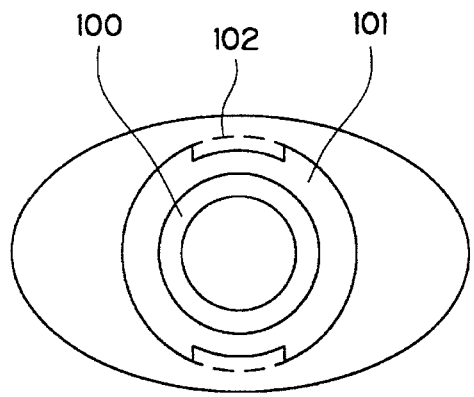
FIG. 6 is a top view of a cap of a self-closing catheter valve, according to one preferred embodiment of this invention.

The exterior shape of the self-closing catheter valve according to one preferred embodiment of this invention is shown in FIGS. 1–3. The exterior shape of the self-closing catheter valve shown in FIGS. 1–3 is formed by a housing 1 having an oval cross-sectional shape, the outer contour of which makes a transition into a conical tip having a circular cross section. The transition from the conical tip to the housing takes place while avoiding any sharp edge lines.

The conical tip comprises the hose attachment connector 2 which can be inserted into a catheter hose. An actuation member 4 is disposed on one of the narrow sides of the housing 1 which is penetrated by a major axis of the oval cross section. According to one preferred embodiment of this invention, the actuation member 4 is a push button. The self-closing catheter valve of the preferred embodiment shown in FIGS. 1–3 does not pose a threat that the patient will rub himself raw on it. The shape also causes the self-closing catheter valve always to rest on a broad side. But because the actuation member 4 is located on a narrow side, an unintentional actuation of the self-closing catheter valve, caused, for example, by the patient lying on top of the self-closing catheter valve, is impossible. The design of the shape also makes the operation by the patient apparent. Because the actuation member 4 can be seen as the only movable part on the outside of the self-closing catheter valve, the patient is inclined to operate the self-closing catheter valve correctly.

The conical hose attachment connector 2 has a cylindrical bore which transitions into a rectangular chamber 6 defined by the housing 1. The rectangular chamber 6 is enclosed by a separating wall 9 having an outlet opening 8, which is aligned with the cylindrical bore 7.

According to one preferred embodiment of this invention, as shown in FIGS. 2 and 3, the hose attachment connector 3 and the housing 1 are made of one piece and the rectangular chamber 6 is closed off by a cap 10 which can be attached to the housing 1 and comprises the separating wall 9. It is apparent that the cap 10 and the housing 1 may be made in accordance with other conventional design techniques known in the plastic-processing industry. A valve hose piece 3, preferably made from a silicon hose, extends through the cylindrical bore 7 of the hose attachment connector 2 through the chamber 6 as far as the separating wall 9. A spring element 5 is positioned in the chamber 6 and is shown in a perspective view in FIG. 3a. As shown in FIG. 3a the spring element 5 is a spring bent into a V-shape, having a first spring leg 11 with a full surface and a second spring leg 12 with a recess 13. The width of the recess 13 is preferably greater than the exterior diameter of the valve hose piece 3. The recess 13 is bordered by an end bar 14 on a free end of the second spring leg 12 and two longitudinal bars of the second spring leg 12 which support the end bar 14. The end bar 14 is rounded to prevent damage to the valve hose piece 3. In the assembled state of the self-closing catheter valve, the first spring leg 11 of the spring element 5 rests against a wall surrounding the chamber 6 opposite the actuation member 4. The valve hose piece 3 is routed below the second spring leg 12 of the spring element 5. As shown in FIG. 3, the valve hose piece 3 protrudes through the recess 13. In the non-actuated state of the self-closing catheter valve, the end bar 14 presses on the valve hose piece 3.

The actuation member 4 is designed as a push button which has two actuation member legs 15 which are parallel, separated, and extend into the chamber 6. The two actuation member legs 15 abut the longitudinal bars of the second spring leg 12 of the spring element 5. The length of the travel of the actuation member 4 is limited by limiting means which are not shown in the drawings. Accordingly, the spring element 5 has a double function. The spring element 5 squeezes the valve hose piece 3 shut by pressing the valve hose piece 3 with the end bar 14 against a wall of the chamber 6 which accommodates the actuation member 4. The spring element 5 also continuously pushes the actuation member 4 hack into a closed position. To prevent the actuation member 4 from being twisted against the wall of the housing 1, front faces 16 of the actuation member legs 15 are rounded. When the bar 14 of the leg 12 is pushed away from the wall against which the valve hose piece 3 rests by applying pressure on the actuation member 4, the entire cross section of the valve hose piece 3 is opened. If the actuation member 4 is released, the actuation member 4 is automatically pushed hack into its initial position and the valve hose piece 3 is again squeezed shut.

The spring element 5 can he made from spring steel, hut other materials may he used as well. If after a period of time the valve hose piece 3 must be replaced, it is only necessary to remove the cap 10 and the valve hose piece can he pulled out. So that in the process of replacing the valve hose piece 3 the spring element 5 does not inadvertently slide out of the chamber 6, it is possible to position appropriate cams in the chamber 6, or the spring element 5 may be fastened by a removable adhesive. The self-closing catheter valve can be easily disassembled for complete sterilization.

The spring element 5 shown in FIGS. 2 to 3a has a linear spring characteristic. Thus, the deformation of the spring element 5 is proportional to the force applied to the spring element 5. To keep the self-closing catheter valve open for draining, a patient must continuously exert maximum pressure on the spring element 5 via the actuation member 4. This is arduous for elderly, easily weakened persons.

FIGS. 12 and 13 show another preferred embodiment of spring element 50 resting in a holder 60. The spring element 50 and the holder 60 can easily be inserted into the chamber 6. The holder 60 is rigid, has the shape of a wide U, and has two parallel legs 61, 62 which are relatively short. The spring element 50 is prestressed between the two parallel legs 61 and 62. The spring element 50 is prestressed because it is bent in the shape of a hairpin and thus has a longer actuation spring arm 51 and a shorter closing spring arm 52, and the length of the actuation spring arm 51 is greater than length of a bed 63 of the holder 60. The actuation spring arm 51 arches over the bed 63 and one end of the actuation spring arm 51 is positioned in a bend between the bed 63 and the shorter parallel leg 61, and another end of the actuation spring arm 51 which forms a hairpin-shaped bend 54 is positioned in a cutout 64.

When pressure P is exerted on the actuation spring arm 51 by actuation member 4, not shown, the spring arm 51 slightly elongates before snapping into an S-shaped form. In this position, as shown in FIG. 13, the spring element can be held by a small force P. The actuation member 4 can snap back into its initial position only when the patient completely releases it. In the process, the shorter closing spring arm 52 pivots along. Thus, in a loaded state of the spring element 50, as shown in FIG. 13, the valve hose piece 3, positioned above the spring element 50, not shown, is completely released, while in an unloaded and prestressed state of the spring element 50, as shown in FIG. 12, an upwardly angled end 53 of the closing spring arm 52 presses the valve hose piece 3 against the chamber wall above the spring element 50.

In the embodiments of this invention previously described the self-closing catheter valve can be operated by the patient and is therefore designed to be self-closing. As a rule, self-closing catheter valves are not used with urine collecting bags. Even though during the day many patients could make do with an automatic catheter, which is not connected to a urine bag, they are provided with a non-automatic catheter valve so that it is not necessary to change the catheter valve at night and to connect a urine bag to it. One preferred embodiment of this invention provides a solution for the problem identified above.

Figure 7:
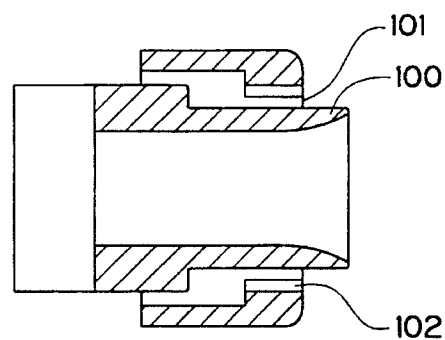
FIG. 7 is a cross-sectional view of the cap shown in FIG. 6, with a mated female plug member.

According to one preferred embodiment of this invention, the cap 10 shown FIGS. 6 and 7 is specially designed, and the actuation member 4 is provided with a locking slide 44. The cap 10 disposed on a urine outlet end of the self-closing catheter valve 10 has a central tube 100 which is formed as one piece with the cap 10 from plastic material. The central tube 100 slightly projects past the cap 10, and a male connector plug, which is connected to the urine bag via a hose, is connected to the cap during use. Preferably, the male connector plug is inserted into an annular conduit 101 which is formed by the cap 10 and surrounds the central tube 100. The size of the annular conduit 101 corresponds to the male plug, which is not shown in the drawings. Two projections 102, disposed on a conduit wall of the annular conduit 101 and located diametrically opposite each other, permit the male plug to be locked in a female plug of the cap 10. Accordingly the male plug has radially outwardly extending projections which interlock with projections 102 after the two plugs have been rotated in relation to each other thereby forming a bayonet coupling. The axial force necessary to keep the plugs locked in a coupled state is provided by a silicon hose which slightly protrudes out of the male plug and is slightly compressed by the female plug.

During the day, the cap 10 of this preferred embodiment can be used as a urine outlet without a hose connection and plugs, the central tube 100 assuring a clean exit in the process. During the night it is only necessary to connect a urine bag with a hose, on which the male plug is fastened.

Figure 9:
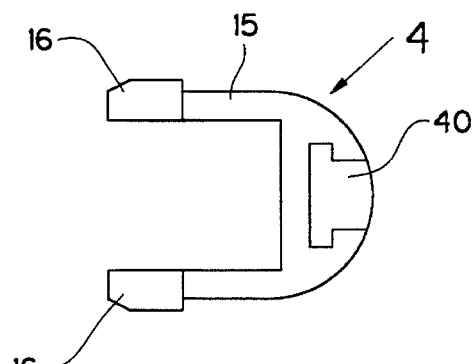
FIG. 9 is a side view of the lockable actuation member shown in FIG. 8.
Figure 11:
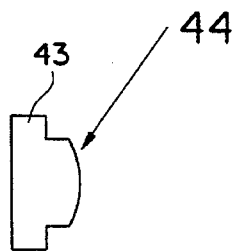
FIG. 11 is a front view of the locking slide shown in FIG. 10.
Figure 10:
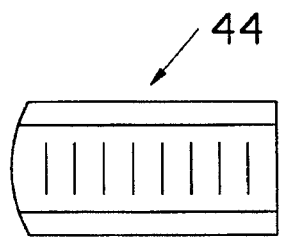
FIG. 10 is a top view of a locking slide which can be mated with the lockable actuation member shown in FIG. 8, according to one preferred embodiment of this invention.

During the night the self-closing catheter valve should remain completely open. According to one preferred embodiment of this invention the actuation member 4 shown in FIGS. 8 and 9 and a locking slide 44 as shown in FIGS. 10 and 11 are used to maintain the self-closing catheter valve in an open position.

Figure 8:
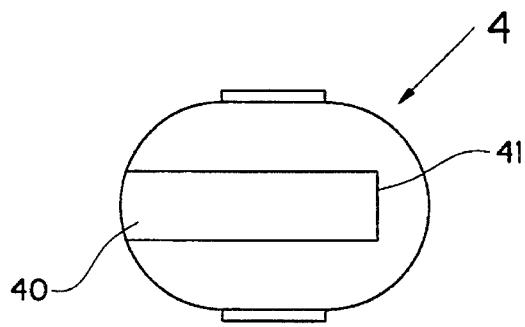
FIG. 8 is a top view of a lockable actuation member, according to one preferred embodiment of this invention.

From FIG. 8 it can be clearly seen that a channel 40 has been cut into the actuation member 4 in the shape of a push button, which is bordered on one side by a stop 41. It can be clearly seen in FIG. 9 that the channel 40 has a T-groove cross section. Care must be taken when mounting the push button 4 that the stop 41 faces toward the cap 10 so that the locking slide 44 positioned in the T-groove-shaped channel 40 can only be pushed in the direction away from the cap 10. The cap 10 is located on the side pointing away from the patient. As a rule, when the patient pushes on the actuation member 4 the patient always has a tendency to exert a force component away from the patient. This causes the locking slide to be pressed against the stop 41, so that no unintentional locking into the open position results. The self-closing catheter valve therefore remains in an automatically closing position. However, if the valve is actuated by a nurse, which is usually the case when the urine bag is connected for the night or must be replaced, the nurse exerts a force component away from the nurse but towards the patient and is therefore inclined to slide the locking slide 44 into a locking position.

An important advantage of the locking feature and urine bag coupling system of the preferred embodiment described above is that it is possible to attach and replace the urine bag without opening the self-closing catheter valve. Thus the danger of possible contamination is drastically reduced.

The preferred embodiment shown in FIGS. 4 and 5 has the same exterior design as the preferred embodiment shown in FIGS. 2 and 3. In contrast to the preferred embodiment shown in FIGS. 2 and 3, the hose attachment connector 2 of the preferred embodiment shown in FIGS. 4 and 5 is separated from the remainder of the housing 1. The remaining housing is a sleeve 1' which is bordered by a separating wall 9 formed by the sleeve 1'. The chamber 6 is located completely inside the sleeve 1'. The bore 7 of the hose attachment connector 2 is aligned with an outlet opening 8 in the separating wall 9. The hose attachment connector 2 has a plug 20 oriented toward the chamber 6, which fits into a corresponding recess of the sleeve 1' in a form-fitting manner and simultaneously closes off the chamber 6 toward the hose attachment connector 2.

An elastically flexible tube 21 adjoins the plug 20 and is aligned with the bore 7. In a longitudinal direction the elastically flexible tube 21 almost completely extends through the chamber 6. An end of the elastically flexible tube 21 is closed off by a valve plate 22. The valve plate 22 has a slightly larger diameter than the exterior diameter of the elastically flexible tube 21. In an area bordering the valve plate 22, the elastically flexible tube 21 has an opening 23 which is directed toward a chamber wall of the chamber 6 which is penetrated by the actuation member 4. The valve hose piece 3 which extends through the chamber 6 as far as the separating wall 9, surrounds the elastically flexible tube 21. The valve hose piece 3 is clamped to the separating wall 9 by a clamping element which is inserted into the outlet opening 8. The actuation member 4 is limited in its length of travel in the direction toward an outside of the housing 1, for example by a ridge at the end of the chamber.

FIG. 4 shows the self-closing catheter valve in a non-actuated closed position. The valve plate 22 slightly spreads open the valve hose piece 3 thereby closing it. The elastically flexible tube 21 is moved away from the wall of the chamber 6 by actuation member 4 and the rubber-elastic hose 3 is deformed so that it arches upward and frees the elastically flexible tube 21 in an area surrounding the opening 23 as shown in FIG. 5. In this way the elastically flexible tube 21 replaces the spring element 5. Accordingly, no separate spring element is required. If the actuation member 4 is released, the elastically flexible tube 21 springs back into its initial position and simultaneously pushes the actuation member 4 back into an initial position. In the initial position the valve plate 22 presses the valve hose piece 3 against a wall surrounding the chamber 6 in which the actuation member 4 is mounted. It is sufficient if the valve hose piece 3 is pressed only on an area which adjoins the opening 23. The chamber wall can have a ridge in the area in which the valve plate 22 rests to increase closing pressure. The ridge prestresses the elastically flexible pipe 21 causing it to rest against the chamber wall.

We claim:

1. In a self-closing catheter valve, including a housing (1) having a chamber and forming a hose attachment connector (2) which can be inserted into a catheter hose, a valve hose piece (3) which at least partially extends through the housing (1), a spring element (5) for deforming the valve hose piece (3) positioned within the chamber (6), and an actuation member (4) for bringing the self-closing catheter valve (1) into an open position, wherein the housing (1) has an oval cross section, and the actuation member (4) actuates the spring element (5) and is slideably mounted along a major axis of the oval cross section within a housing wall opening, the improvement comprising: a first spring leg (11) of the spring element (5), a second spring leg (12) of the spring element (5), the first spring leg (11) and the second spring leg (12) arranged to form a V-shape, the first spring leg (11) abutting the housing (1), the second spring leg (12) having a recess (13) wide enough to accommodate the valve hose piece (3), the second spring leg (12) having a free end portion, the second spring leg (12) having an end bar (14) located at the free end portion and two longitudinal bars each connected to the end bar (14), the recess (13) being bordered by the two longitudinal bars and the end bar (14), the end bar (14) urging the valve hose piece (3) against the housing (1), and the actuation member (4) comprising a button which is abuttable against the two longitudinal bars.

2. In a self-closing catheter valve in accordance with claim 1, wherein the housing (1) further comprises two plastic sections, one section of the two plastic sections having the hose attachment connector (2) and the chamber (6), another section of the two plastic sections which is connected with the one section comprising a cap (10) which closes the chamber (6) and which has an opening (8) in which an end of the valve hose piece (3) is fastened.

3. In a self-closing catheter valve in accordance with claim 1, further comprising a housing wall positioned opposite from the hose attachment connector (2) having a plug element (100, 101, 102) for connection with a suitable hose plug.

4. In a self-closing catheter valve in accordance with claim 3, wherein the plug element (100, 101, 102) is positioned in the housing (1) and comprises a central tube (100), an annular conduit (101) having a plurality of radially inward directed projections (102), and the annular conduit (101) surrounding the central tube (100).

5. In a self-closing catheter valve in accordance with claim 1, further comprising a locking slide (44) displaceably seated in the actuation member (4), and the actuation member (4) lockable in a position in which the valve is open.

6. In a self-closing catheter valve in accordance with claim 1, further comprising a holding element (60) having a base 63 and two legs (61, 62), the spring element (50) being prestressed in the holding element (60) and bent into a shape of a hairpin, and a longer actuation spring arm (51) of the spring element (50) between the two legs (61, 62) arched in a prestressed condition over the base (63) of the holding element (60) in an unloaded state of the spring element (50) and the longer actuation spring arm (51) springing into an S-shape upon a pressure force applied to the spring element (50).

7. In a self-closing catheter valve including a housing (1) having a chamber and forming a hose attachment connector (2) which can be inserted into a catheter hose, a valve hose piece (3) which at least partially extends through the housing (1), a spring element (5) for deforming the valve hose piece (3) positioned within the chamber (6), and an actuation member (4) for bringing the self-closing catheter valve (1) into an open position, wherein the housing (1) has an oval cross section, and the actuation member (4) actuates the spring element (5) and is slideably mounted along a major axis of the oval cross section within a housing wall opening, the improvement comprising: a first spring leg (11) of the spring element (5), a second spring leg (12) of the spring element (5), the first spring leg (11) and the second spring leg (12) arranged to form a V-shape, the first spring leg (11) abutting the housing (1), the second spring leg (12) having a recess (13) wide enough to accommodate the valve hose piece (3), the second spring leg (12) having a free end portion, the second spring leg (12) having an end bar (14) located at the free end portion and two longitudinal bars each connected to the end bar (14), the recess (13) being bordered by the two longitudinal bars and the end bar (14), the end bar (14) urging the valve hose piece (3) against the housing (1), the actuation member (4) comprising a button which is abuttable against the two longitudinal bars, the actuation member (4) having a channel (40) in a form of a T-groove, the channel (40) having an opening in a direction toward the hose attachment connector (2), and the actuation member (4) having a stop face (41) within the channel (40) opposite the opening, and a locking slide (44) slidingly seated in the channel (40).

* * * * *